United States Patent [19]

Roth et al.

[11] Patent Number: 4,946,456
[45] Date of Patent: Aug. 7, 1990

[54] FLUID IMBIBING PUMP ACTIVATED BY CAPILLARY ACTION OF A FABRIC OR POLYMERIC SLEEVE

[75] Inventors: Nathan Roth, San Francisco; Su I. Yum; Felix, Theeuwes, both of Los Altos, all of Calif.

[73] Assignee: Alza Corp., Palo Alto, Calif.

[21] Appl. No.: 236,868

[22] Filed: Aug. 26, 1988

[51] Int. Cl.$^5$ ............................................. A61K 9/22
[52] U.S. Cl. ................................................. 604/892.1
[58] Field of Search ...................... 604/892.1; 128/126, 128/145, 151

[56] References Cited

U.S. PATENT DOCUMENTS

| | | |
|---|---|---|
| 3,760,984 | 9/1973 | Theeuwes . |
| 3,987,790 | 10/1976 | Eckenhoff et al. . |
| 3,995,631 | 12/1976 | Higuchi et al. . |
| 4,034,756 | 7/1977 | Higuchi et al. . |
| 4,474,575 | 10/1984 | Eckenhoff et al. . |
| 4,539,004 | 9/1985 | Eckenhoff et al. . |
| 4,723,958 | 2/1988 | Pope et al. ......................... 604/892.1 |

Primary Examiner—Alan W. Cannon
Assistant Examiner—Natalie Paul
Attorney, Agent, or Firm—D. Byron Miller; Edward L. Mandell; Steven F. Stone

[57] ABSTRACT

An agent dispenser of the fluid imbibing type having a flexible bag within a membrane and in which a wicking or wetting device is in contact with the outer surface of the membrane to keep such outer surface wet at all times for all attitudes of a containment vessel housing the bag and the membrane. The wicking device is in the form of a fabric tube, such as a stretch knit fabric, or a preformed hydrophilic polymeric sleeve, which can be mounted on the outer surface of the membrane and remain in contact with it so long as there is any liquid in the containment vessel. Since the amount of water drawn by the wicking device is controlled by the membrane porosity and the amount of a solute composition in an intermediate layer between the bag and the membrane, the wicking device provides for a continuous controlled delivery of agent from the inner bag of the dispenser.

30 Claims, 1 Drawing Sheet

FLUID IMBIBING PUMP ACTIVATED BY CAPILLARY ACTION OF A FABRIC OR POLYMERIC SLEEVE

BACKGROUND OF THE INVENTION

Field of the Invention

This invention relates to agent dispensers of the fluid imbibing type, such as those which are driven osmotically and, more particularly, to an improvement for such an agent dispenser to render it suitable for continuous operation.

The invention is an improvement over agent dispensers described in U.S. Pat. Nos 3,760,984, 3,987,790, 3,995,631, 4,034,756, 4,474,575 and 4,539,004, all of which are incorporated herein by reference. In each of these patents, an agent dispenser is disclosed which is osmotically driven and whose size renders it suitable for use as a therapeutic system for administering agents to animals and humans. The dispenser includes an inner agent receiving means, such as a flexible bag that holds an agent to be dispensed, an intermediate fluid imbibing means such as a layer of an osmotically effective solute composition, for example, an inorganic salt, and an outer membrane that is permeable to fluid such as water and encapsulates both the bag and the solute layer. The bag has a discharge port which allows the agent to be directed to a location of use.

The agent dispenser is actuated by filling the bag with a flowable agent to be dispensed and by placing the dispenser in an environment, such a body cavity or a containment vessel. Fluid, typically water, is imbibed from the environment by the solute through the membrane and into the space between the inner bag and the membrane. The imbibed fluid squeezes the bag inwardly, thereby displacing the agent out of the discharge port.

A drawback in the use of all prior agent dispensers of the aforesaid type, particularly when used within a fluid containment vessel, is that the dispensers have been dependent upon either over-filling the containment vessel or maintaining the vessel and the dispenser in one operational attitude. Thus, as the driving fluid in the containment vessel becomes depleted, a portion of the outer surface of the membrane can be out of contact with the driving fluid for a particular attitude of the dispenser, thereby causing a change in the flow rate of the agent out of the internal bag. This change in operation of the agent dispenser cannot be tolerated in many instances, and a need exists for improving the agent dispenser such that it can compensate for changes in the attitude or operative position of the agent dispenser and containment vessel. The present invention satisfies this need.

DEFINITION OF TERMS

The expression "agent" as used herein denotes any drug or agent administered to produce a nutritional, therapeutic or other desired effect including for example: composition in any way affecting any biological entity; substance having a nutrient or stimulating action or growth inhibiting, destroying or any regulating action on plant growth, controlled or otherwise; substance to be assimilated by any organism, e.g., human being, animal, or lower order organism, for its nourishment or for regulating its growth; substance exhibiting any of the above activities to be directly applied to the habitat, surroundings or environment of any of the above organisms; and substance having any other effect on any other environment, especially any aqueous environment.

Therefore, suitable agents for use with the dispenser of this invention include, without limitation, those which are generally capable of:

1. Preventing, alleviating, treating or curing abnormal or pathological conditions of the living body by such means as destroying a parasitic organism or limiting the effect of the disease of abnormality by chemically altering the physiology of the host of parasite;
2. Maintaining, increasing, decreasing, limiting or destroying a physiologic body or plant function, e.g., vitamin compositions, set sterilants, fertility inhibitors, fertility promoters, growth promoters, and the like;
3. Diagnosing a physiological condition or state;
4. Controlling or protecting an environment or living body by attracting, disabling, inhibiting, killing, modifying, repelling or retarding an animal or microorganism, such as food and non-food baits, attractants and lures, biocides, pesticides, algicides, parasiticides, rodenticides, insecticides, fungicides, and the like;
5. Preserving, disinfecting or sterilizing; and
6. Controlling or affecting generically an environment, as by introducing a catalyst or metering a reactant into a reacting chemical system, or by effecting any chemical process therein, such as a fermentation, including propagation and/or attenuation of a microorganism.

The term "environment" as used herein denotes any prospective situs for the dispenser of this invention, or at least for the external fluid permeable membrane component thereof, which is comprised of or will provide sufficient fluid, e.g., water, for absorption into the dispenser to develop the needed osmotic pressure on which its motive force depends; and implicit in the foregoing definition of "agent"—one that will develop its action in the presence of such an environment, or one that will develop its action on a remote and/or another environment, which need not be fluid or aqueous.

SUMMARY OF THE INVENTION

The present invention is directed to an improvement in agent dispensers of the type described in which a wicking or wetting device is in contact with the outer surface of the membrane to keep such outer surface wet at all times for all attitudes of the containment vessel so long as there is driving fluid in the vessel. To this end, this wicking device preferably is in the form of a fabric tube, such as a stretch knit fabric, or a preformed hydrophilic polymeric sleeve, which can be mounted on the outer surface of the membrane and remain in contact with it so long as there is any fluid in the containment vessel. Thus, the delivery of agent from the inner bag will be substantially continuous regardless of the attitude of the containment vessel and the agent dispenser therein.

Moreover, the designs of the containment vessel and the wicking tube are such that the system is sealed against any liquids entering through the exit port of the inner bag. Also, this design modification prevents the entry of water from the containment vessel into the bag itself. Since the amount of fluid drawn by the knit fabric tube is controlled by the membrane porosity and the amount of solute composition in the intermediate layer, the assembly provides for a continuous controlled delivery of agent from the inner bag of the dispenser. Moreover, the system shutdown time can be controlled by the amount of fluid placed in the containment vessel.

The primary object of the present invention is to provide an improved osmotically actuated agent dispenser in a sealed containment vessel wherein the dispenser includes an agent receiving means such as an inner bag encapsulated by a porous membrane having a wetting means thereon for keeping the outer surface of the membrane wet so as to provide for a continuous delivery of agent from the inner bag regardless of the attitude of the dispenser and the containment vessel so long as a driving fluid is in the containment vessel.

Other objects of this invention will become apparent as the following specification progresses, reference being had to the accompanying drawings for an illustration of the invention.

DETAILED DESCRIPTION OF THE INVENTION

Figure 3:
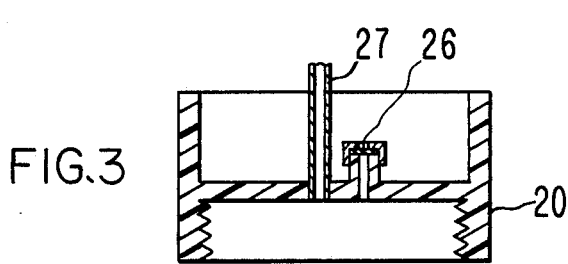
FIG. 3 is a cross-sectional view of another embodiment of an end cap of the assembly of FIGS. 1 and 2.
Figure 2:
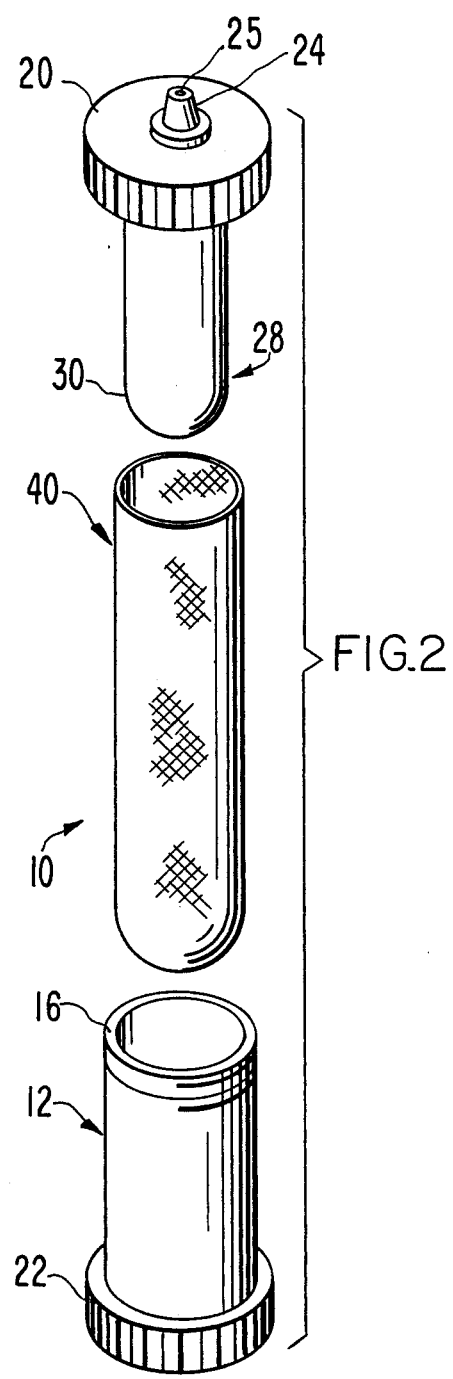
FIG. 2 is an exploded, perspective view of the assembly of the pump assembly.
Figure 4:
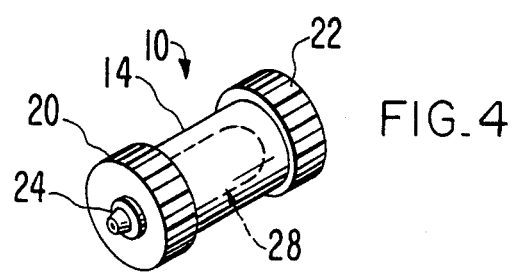
FIG. 4 is a perspective view of the pump assembly, showing the parts assembled together as a unit.

A fluid imbibing pump assembly of the present invention is broadly denoted by the numeral 10 and includes a containment vessel 12 having a generally cylindrical sidewall 14 and provided with threaded, open ends 16 and 18 for threadably receiving end caps 20 and 22. End cap 20 typically has a luer fitting 24, the cap 20 having a threaded hole for accepting the fitting 24. In an alternate embodiment of cap 20 as shown in FIG. 3, the cap is provided with a rubber septum 26 adjacent to an agent discharge tube 27.

Assembly 10 further includes an agent dispenser 28 in the form of an osmotic pump. The agent dispenser 28 includes an outer, rigid, shape-retaining casing 30 in the form of a tube at least a portion of which is a semipermeable membrane, an intermediate fluid imbibing means such as osmotically active sleeve 32, and an inner agent receiving means such as collapsible bag 34. The agent dispenser 28 is of the type described in commonly owned U.S. Pat. Nos. 3,987,790, 3,995,631 and 4,034,756. The agent to be dispensed is in a flowable form, preferably in a gel, paste, or other semi-solid state, albeit a solution or concentrated solution of agent will sometimes suffice.

Figure 1:
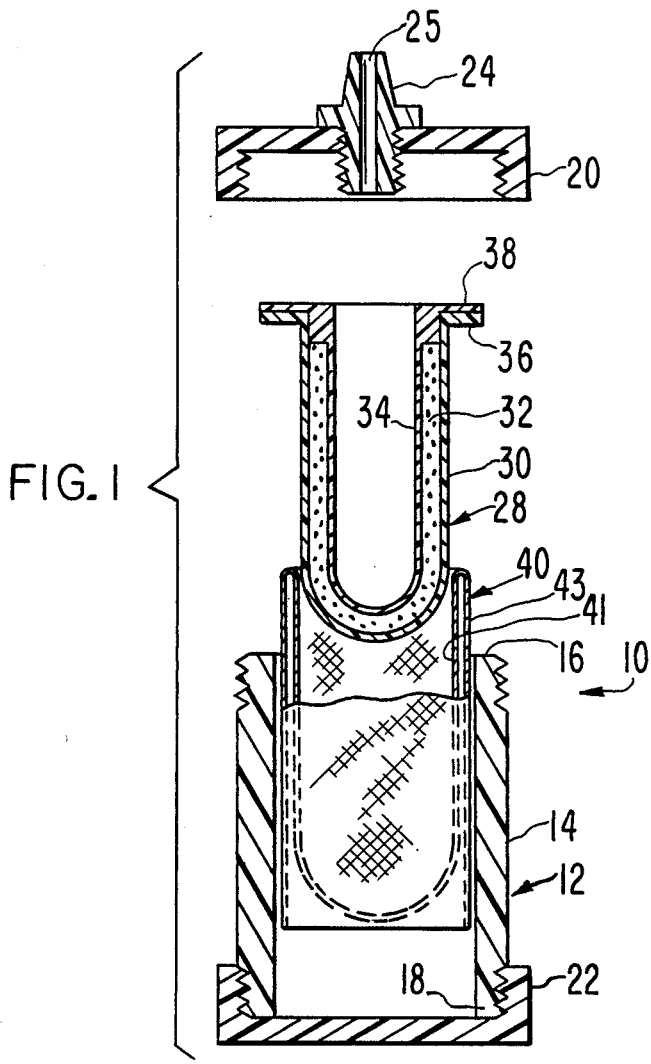
FIG. 1 is an exploded view, in cross-section, of a fluid imbibing pump assembly having a fabric sleeve over the outer surface of an agent dispenser within a containment vessel.

Membrane 30 is tubular and has an upper, annular flange 36 which is adapted to be mated with the upper flange 38 on bag 34 as shown in FIG. 1. Flanges 36 and 38 present a seal which prevents flow of agent from bag 34 into the space within containment vessel 12 (i.e., the space surrounding dispenser 28. Sleeve 32 includes an osmotically effective solute, such as an inorganic salt. The agent dispenser 28 is adapted to be received within containment vessel 12 and to be subjected to a fluid directed into the vessel through end 18 when cap 22 is off wall 14.

In operation, bag 34 is filled with an agent, such as a drug, to be dispensed and the agent dispenser 28 is placed in the fluid environment of containment vessel 12, water typically being the fluid. Water is imbibed from the environment within vessel 12 by the water imbibing composition in sleeve 32, the water flowing through the membrane 30 into the space between the membrane and bag 34 which is the space occupied by sleeve 32. Since the membrane 30 is rigid and the bag 34 is collapsible, the bag 34 is squeezed inwardly in response to the influx of water into the space occupied by sleeve 32, thereby displacing or pumping the agent out of bag 34 by way of port 25 in luer fitting 24. The permeability of membrane 30 to water controls the rate at which water is imbibed from the environment within vessel 12 and this also affects the rate in which the agent in bag 34 is pumped from the dispenser 28. The permeability is, in turn, a function of the composition and thickness of membrane 30. The time period over which agent is dispensed from bag 34 depends upon the volume of agent in the bag and the rate at which it is pumped therefrom.

All of the foregoing structural elements of dispenser 28 have been known and used in the past. The improvement of the present invention is the use of a wet bulb sock in the form of an absorbent member, such as a fabric tube 40, placed over and about membrane 30 so that the water in the containment vessel 12 is drawn up or absorbed into the fabric material of tube 40 thereby wetting substantially the entire outer surface of membrane 30.

While a single layer of tube 40 can be satisfactorily used to wet the outer surface of membrane 30 with the water from vessel 12, it is preferred that a double layer of tube 40 be provided to cover membrane 30. To this end, the length of tube 40 will be typically twice the length of membrane 30 so that after a single layer 41 is placed over the membrane, a second layer 43 will be doubled upon and engage the first layer and cover the first layer.

Any suitable material can be used to form tube 40. For instance, an absorbent grade of cotton can be used. The cotton can also be a stretchable knit material. Also suitable for tube 40 are hydrophilic polymers, as are known in the art.

In forming assembly 10, tube 40 is first placed over membrane 30 so that the entire outer surface of the membrane is effectively covered and contacted by tube 40. Then the mating flanges 36 and 38 are placed in cap 20, the agent dispenser 28 with fabric tube 40 thereon is inserted into end 16 of containment vessel 12, and cap 20 is threaded into place on end 16. Cap 22 is removed and water or other driving fluid is directed into vessel 12 to a precalibrated line (not shown) on the vessel. Cap 22 is then threaded into place and upon being sealed, assembly 10 is activated.

The water in vessel 12 is drawn up into tube 40 and placed in contact with the outer surface of membrane 30. The solute sleeve 32 draws moisture through membrane 30, swelling the solute sleeve and compressing the filled agent reservoir, namely bag 34. The compressed bag 34 causes the agent to be displaced out of the bag through port 25 or through a discharge tube coupled with the port. Since the amount of water drawn by the tube 40 is controlled by membrane 30 and the solute content of sleeve 32, assembly 10 is operable to deliver a controlled, continuous supply of agent from bag 34. The shutdown time of assembly 10 can be controlled by the amount of fluid placed in vessel 12.

Optionally, the threaded parts can be solvent or heat welded in high speed filling machines. Also, optionally, one of the parts, for instance the caps can contain a rubber flange for injection of the water in vessel 12. A vent can also be added to facilitate filling of driving agent. A flow moderator can be used as an optional feature. Filling of bag 34 can be done through the exit port 25.

By using tube 40 on membrane 30, assembly 10 will function in any position or attitude, such as tilted, upright, and all other positions until the depletion of the water supply in vessel 12 is complete. Thus, even if a portion of the membrane 30 is above the fluid level in the vessel 12, the entire outer surface of the membrane will still be wet by virtue of the wicking or capillary action of tube 40.

We claim:

1. A fluid imbibing pump assembly particularly adapted for operation with a containment vessel for the pump and a driving fluid for said pump, said pump comprising, in combination:
    a fluid imbibing pump having an outer, generally rigid casing, at least a portion of which is semipermeable to said driving fluid; and
    a fluid absorbent material coupled with said fluid imbibing pump for wetting the semipermeable portion of said casing for all operative positions of said containment vessel.

2. The assembly as set forth in claim 1, wherein said fluid absorbent material includes a wick.

3. The assembly as set forth in claim 2, wherein said wick is in the form of a tube.

4. The assembly as set forth in claim 2, wherein said wick is in the form of a knit fabric and the rigid casing comprises a semipermeable membrane.

5. The assembly as set forth in claim 4, wherein the fabric is in the form of a tube for surrounding the membrane.

6. The assembly as set forth in claim 5, wherein the length of the tube is at least equal to the length of the membrane.

7. The assembly as set forth in claim 5, wherein the length of the tube is greater than the length of the membrane.

8. The assembly as set forth in claim 5, wherein the tube is in the form of a double layer of fabric material, one end of the inner layer being closed.

9. The assembly as set forth in claim 1, wherein said wetting means is a preformed hydrophilic polymeric sleeve.

10. An agent dispenser assembly comprising, in combination:
    a containment vessel adapted to contain a fluid imbibing pump and a driving fluid for said pump;
    a fluid imbibing pump within said containment vessel, said fluid imbibing pump having an outer, generally rigid casing, at least a portion of which is semipermeable to said driving fluid; and
    a fluid absorbent material coupled with said fluid imbibing pump for wetting the semipermeable portion of said casing for all operative positions of said containment vessel.

11. The assembly as set forth in claim 10 wherein said fluid absorbent material includes a wick.

12. The assembly as set forth in claim 11, wherein said wick is in the form of a tube.

13. The assembly as set forth in claim 13, wherein said wick is in the form of a knit fabric and the rigid casing comprises a semipermeable membrane.

14. The assembly as set forth in claim 13, wherein the fabric is stretchable and in the form of a tube surrounding the membrane.

15. The assembly as set forth in claim 13, wherein the length of the tube is at least equal to the length of the membrane.

16. The assembly as set forth in claim 13, wherein the length of the tube is greater than the length of the membrane.

17. The assembly as set forth in claim 13, wherein the tube is in the form of a double layer of fabric material, one end of the inner layer being closed.

18. The assembly as set forth in claim 10 wherein said fluid absorbent material is a preformed hydrophilic polymeric sleeve.

19. The assembly as set forth in claim 10, wherein the fluid imbibing pump includes a collapsible bag adapted to contain a flowable agent, the casing and the bag having respective end flanges in mating engagement with each other.

20. An agent dispenser assembly comprising, in combination:
    a containment vessel having an open end, a cap for removably closing the open end and an outlet means for said vessel;
    a fluid imbibing pump removably received within said containment vessel, said fluid imbibing pump having an outer rigid casing at least a portion of which is semipermeable to a driving fluid, said pump having an outlet means communicating with the outlet means of said containment vessel to allow agent to be dispensed from the pump; and
    a fluid absorbent material coupled with the membrane for wetting the outer surface thereof for all operative attitudes of the agent dispenser.

21. The assembly as set forth in claim 20, wherein said fluid absorbent material includes a wick.

22. The assembly as set forth in claim 21, wherein said wick is in the form of a tube.

23. The assembly as set forth in claim 21, wherein said wick is in the form of a knit fabric and the rigid casing comprises a semipermeable membrane.

24. The assembly as set forth in claim 23, wherein the fabric is in the form of a tube surrounding the membrane.

25. The assembly as set forth in claim 24, wherein the length of the tube is at least equal to the length of the membrane.

26. The assembly as set forth in claim 24, wherein the length of the tube is greater than the length of the membrane.

27. The assembly as set forth in claim 24, wherein the tube is in the form of a double layer of fabric material, one end of the inner layer being closed.

28. The assembly as set forth in claim 20, wherein said fluid absorbent material is a preformed hydrophilic polymeric sleeve.

29. The assembly as set forth in claim 20, wherein the fluid imbibing pump includes a collapsible bag adapted to contain a flowable agent, the casing and the bag having respective end flanges in sealing engagement with each other and with the cap.

30. A fluid imbibing pump assembly including a fluid imbibing pump adapted for operation within a containment vessel which contains a driving fluid for the pump, said pump having an outer, generally rigid casing which is semipermeable and permeable to the driving fluid; and a fluid absorbent member covering the entire semipermeable rigid casing, whereby the fluid absorbent member absorbs the driving fluid and wets the entire semipermeable rigid casing for all operative positions of the containment vessel and the fluid imbibing pump imbibes the driving fluid at a substantially constant rate for all operative positions of the containment vessel.

* * * * *